(12) United States Patent
Baird et al.

(10) Patent No.: US 10,286,225 B2
(45) Date of Patent: *May 14, 2019

(54) LED PHOTOTHERAPY DEVICE FOR CELL REJUVENATION

(71) Applicant: LED Intellectual Properties, LLC, Irvine, CA (US)

(72) Inventors: Craig Baird, VanCouver (CA); Stan Stanbridge, Costa Mesa, CA (US)

(73) Assignee: LED Intellectual Properties, LLC, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/731,561

(22) Filed: Jun. 5, 2015

(65) Prior Publication Data

US 2015/0265846 A1    Sep. 24, 2015

Related U.S. Application Data

(63) Continuation-in-part of application No. 12/205,199, filed on Sep. 5, 2008, now Pat. No. 9,079,022.

(Continued)

(51) Int. Cl.
*A61N 5/06* (2006.01)

(52) U.S. Cl.
CPC .......... *A61N 5/0616* (2013.01); *A61N 5/0617* (2013.01); *A61N 2005/0632* (2013.01);
(Continued)

(58) Field of Classification Search
CPC ................ A61N 5/0616; A61N 5/0617; A61N 2005/0632; A61N 2005/0644;
(Continued)

(56) References Cited

U.S. PATENT DOCUMENTS 4,930,504 A    6/1990  Diamantopoulos et al.
5,259,380 A   11/1993  Mendes et al.
(Continued)

FOREIGN PATENT DOCUMENTS

WO    2004105586 A2   12/2004
WO    2005086846 A2    9/2005

OTHER PUBLICATIONS

Lumileds Lighting US., LLC. "Technical Datasheet D505—SuperFlux LEDs" , 2005.*

(Continued)

*Primary Examiner* — Rex R Holmes
*Assistant Examiner* — Vynn V Huh
(74) *Attorney, Agent, or Firm* — Law Firm of Stuart S. Levy; Stuart S. Levy (57) ABSTRACT

A light therapy device including multiple light-emitting diodes (LEDs) positioned in a handheld, portable device is disclosed. The device including the LEDs are configured to have direct or nearly direct contact with the skin or tissue of the user without any intermediary materials, and light the surface and underlying layers of tissue for photodynamic stimulation of the user's cells. Housings for the devices may contain an arrangement of 12-600 LEDs on one or more circuit boards in an arrangement to provide even lighting over the skin or tissue surface. A plurality of devices may be connected together for treating larger areas of tissue. A belt may be used for keeping in position a plurality of therapeutic devices.

11 Claims, 11 Drawing Sheets

Related U.S. Application Data (60) Provisional application No. 60/995,696, filed on Sep. 28, 2007, provisional application No. 60/995,703, filed on Sep. 28, 2007, provisional application No. 60/995,705, filed on Sep. 28, 2007.

(52) U.S. Cl.
CPC ............... *A61N 2005/0644* (2013.01); *A61N 2005/0652* (2013.01); *A61N 2005/0659* (2013.01); *A61N 2005/0662* (2013.01); *A61N 2005/0663* (2013.01)

(58) Field of Classification Search
CPC .... A61N 2005/0652; A61N 2005/0659; A61N 2005/0662; A61N 2005/0663
USPC ...................................................... 607/88–94
See application file for complete search history.

(56) References Cited

U.S. PATENT DOCUMENTS

| | | | |
|---|---|---|---|
| 5,278,432 A | 1/1994 | Ignatius et al. | |
| 5,358,503 A | 10/1994 | Bertwell et al. | |
| 5,698,866 A | 12/1997 | Doiron et al. | |
| 5,728,090 A | 3/1998 | Martin et al. | |
| 6,267,779 B1 | 7/2001 | Gerdes | |
| 6,471,716 B1 | 10/2002 | Pecukonis | |
| 6,596,016 B1 | 7/2003 | Vreman et al. | |
| 6,602,275 B1 | 8/2003 | Sullivan | |
| 6,645,230 B2* | 11/2003 | Whitehurst | A61N 5/0613 607/88 |
| 6,762,563 B2 | 7/2004 | St-Germain et al. | |
| 6,828,576 B2 | 12/2004 | Spivak | |
| 6,860,896 B2 | 3/2005 | Leber et al. | |
| 7,081,128 B2 | 7/2006 | Hart et al. | |
| 7,125,416 B2 | 10/2006 | Kent et al. | |
| 7,131,990 B2 | 11/2006 | Bansal et al. | |
| 7,175,587 B2 | 2/2007 | Gordon et al. | |
| 7,204,846 B2 | 4/2007 | Suzuki | |
| 7,267,673 B2 | 9/2007 | Pilcher et al. | |
| 7,317,287 B2 | 1/2008 | Blumel | |
| 7,411,174 B2 | 8/2008 | Eash | |
| 2003/0004499 A1* | 1/2003 | McDaniel | A61B 18/203 606/3 |
| 2003/0187486 A1 | 10/2003 | Savage, Jr. et al. | |
| 2003/0233138 A1 | 12/2003 | Spooner | |
| 2004/0030370 A1 | 2/2004 | Lytle | |
| 2004/0031370 A1 | 2/2004 | Ueno et al. | |
| 2004/0147984 A1 | 7/2004 | Altshuler et al. | |
| 2004/0193234 A1 | 9/2004 | Butler | |
| 2004/0230259 A1 | 11/2004 | Di Matteo | |
| 2005/0085875 A1 | 4/2005 | Van Zuylen | |
| 2006/0020308 A1 | 1/2006 | Muldner | |
| 2006/0030908 A1 | 2/2006 | Powell et al. | |
| 2006/0212025 A1 | 9/2006 | McDaniel | |
| 2006/0287696 A1* | 12/2006 | Wright | A61N 5/0613 607/88 |
| 2007/0032843 A1 | 2/2007 | Hsu | |
| 2007/0106347 A1 | 5/2007 | Lin | |
| 2007/0179570 A1 | 8/2007 | De Taboada et al. | |
| 2007/0198004 A1 | 8/2007 | Altshuler et al. | |
| 2007/0276455 A1* | 11/2007 | Fiset | A61C 19/066 607/91 |
| 2008/0058783 A1 | 3/2008 | Altshuler et al. | |
| 2008/0103563 A1 | 5/2008 | Powell et al. | |
| 2010/0049180 A1* | 2/2010 | Wells | A61N 5/0616 606/12 |

OTHER PUBLICATIONS

Office Action dated Oct. 16, 2014 for U.S. Appl. No. 12/205,199, 11 pages.

Office Action dated Apr. 26, 2013 for U.S. Appl. No. 12/205,199, 12 pages.

Office Action dated Aug. 31, 2012 for U.S. Appl. No. 12/205,199, 11 pages.

* cited by examiner

| Purpose 25 | LED IDENTIFER | | | | |
|---|---|---|---|---|---|
| | 21 ○ | 22 ● | 23 ⊖ | 24 ⦿ | ⊘ |
| Skin Rejuvenation | 850-855 | 660 | 630 | 605 | 605 |
| Reduction of Rosacea | | 850-855 | 660 | 630 | 460-465 |
| Reduction of Acne | 850-855 | 660 | 460-465 | 460-465 | 660 |

FIG. 6

| LED Intellectual Properties |||
| --- | --- | --- |
| Light Wavelength | Forward Voltage | Viewing Angle |
| 415nm or 460-465nm | 2.8 - 4.0 V | 15 - 30° |
| 605nm | 1.8 - 2.6V | 20 - 40° |
| 630nm | 1.8 - 2.8V | 20 - 40° |
| 660nm | 1.5 - 2.2V | 15 - 30° |
| 850-855nm | 1.2 - 2.9V | 15 - 30° |
| 940nm | 1.0 - 1.6V | 15 - 30° |

LED PHOTOTHERAPY DEVICE FOR CELL REJUVENATION

CROSS-REFERENCE TO RELATED APPLICATIONS

This application is a continuation-in-part of applicant's co-pending application U.S. patent application Ser. No. 12/205,199 filed Sep. 5, 2008, entitled LED BASED PHOTOTHERAPY DEVICE FOR PHOTOREJUVENATION OF CELLS which claims priority to Provisional Application 60/995,479 filed Sep. 27, 2007; Provisional Application 60/995,696 filed Sep. 28, 2007; Provisional Application 60/995,703 filed Sep. 28, 2007; and Provisional Application 60/995,705 filed Sep. 28, 2007.

BACKGROUND OF THE INVENTION

Field

Exemplary embodiments of the invention generally relate to light therapy, and more particularly to a therapy system utilizing light emitting diodes as a source of bio-stimulative, non-coherent, non-monochromatic light.

Exemplary embodiments relate to improvements in medical devices for topical photodynamic therapy (POT) treatment to patient's, and particularly to a rigid surface (circuit board) containing light emitting diodes (LEDs) as a source of bio-stimulative, non-coherent, non-monochromatic light, which is placed in contact with or in close proximity with the patient's skin or tissue, and a method for making the medical device or devices.

Description of the Related Art

Non-monochromatic light as defined wavelengths has produced beneficial bio-stimulative effects and has been known to trigger specific biological functions; such as, increased rate of metabolism, photo-repair and cell division. Stimulation occurred, however, with light emitted in specific wavelengths.

While the exact mechanism by which the beneficial bio-stimulative effects have been achieved is not precisely known, several theories have been put forth. It has been suggested that non-monochromatic light across different wavelengths penetrates body tissue and is absorbed, reflected and scattered to excite molecules within cells and tissue to thereby accelerate repair and regeneration. A further theory suggested that different cells had different photoreceptors, which only respond to particular wavelengths of light. This theory supported the phenomenon that the application of only certain wavelengths of light resulted in bio-stimulative effects, the resulting stimulation of the dermis and an increase in production of collagen and elastin.

Light therapy has utilized lasers with relatively low power, and bio-stimulative treatment utilizing lasers has been referred to as "soft" laser therapy. In such applications, low level laser energy radiation has been successfully employed to stimulate wound healing and treatment of musculoskeletal disorders and skin ulcers.

It has been previously theorized that the properties of laser radiation, which resulted in the beneficial bio-stimulative effects of soft laser therapy, were the monochromaticity and coherence of laser radiation.

It occurred to applicants that if bio-stimulative light effects could be compounded by combining into one device 4 different wavelengths of light each with known benefits, that the effects could be greater than if each wavelength was applied separately and close proximity of the LEDs were such that this promoted uniform coverage of the target area to simultaneously receive all wavelengths.

U.S. Patent application 2006/0020308, published on Jan. 26, 2006 to James Scott Muldner, discloses a light therapy device heat management device. The disclosed device uses transmitted thermal energy with different colored LED's to stimulate skin. While this product uses a combination of light and heat, the heat is generated from heating pads and the heat is blown through the device to heat the skin. While this patent application discloses heating along with the light therapy, the heating is generated from a thermal heater as opposed to generating heat by overdriving the lighting (LED's).

U.S. Patent application 2008/0103563, published on May 1, 2008 to Steven D. Powell, discloses a light therapy personal care device. The device combines light therapy with an exfoliating pad or a razor. While this invention uses light therapy, there is no heating of the skin that will open pores to further improve skin condition.

U.S. Pat. No. 6,602,275, issued Aug. 5, 2003 to Jana Sullivan, discloses a device and method for therapeutic treatment of living organisms. The device has a plurality of different colored LED's in combination with a heating or cooling pad. While this patent discloses heating with LED's, the heating is from a separate thermal pad that is placed on the skin prior to or after the light therapy.

U.S. Pat. No. 5,358,503, issued Oct. 25, 1994 to Dale E. Bertwell et al, discloses a light therapy device with LED's that are heated with resistors. The LED's conduct the heat from the resistors to the skin. While this patent discloses light therapy with heating, the heating is provided with resistors and conducted through the LED's.

What is needed is a light therapy device that generates thermal heat that is conducted onto a user's skin. The invention provides this solution and other benefits in hand-held and mountable devices.

SUMMARY OF THE INVENTION

A tissue therapy device may include at least one enclosure; at least one circuit board secured within said at least one enclosure; said circuit board including an array of a plurality of different wavelength light emitting diodes configured to provide photodynamic stimulation of a surface and underlying layers of cells of skin tissue, wherein the stimulation of cells increases production of collagen and elastin; a power jack that receives DC power and a power switch electrically connected to said array of light emitting diodes though a current limiting circuit to said plurality of different wavelength light emitting diodes; said current limiting circuit and a voltage supplied to said power jack is selected so that at least one of said plurality of different wavelength light emitting diodes is overdriven to increase light output of said light emitting diodes beyond normal operating intensity and to further produce thermal heat from said light emitting diodes, wherein the current limiting circuit consistently limits the current of one or more of the plurality of different wavelength light emitting diodes to produce a skin temperate of between 97 and 106 degrees Fahrenheit from direct thermal conduction of said thermal heat from said light emitting diodes which are against or in close proximity to said skin tissue for a predetermined period of time.

The light emitting diodes may transmit light in wavelengths selected from the group consisting of: the wavelengths of 415 nm and 630 nm, the wavelengths of 415 nm and 625 nm and 630 nm, and the wavelengths of 415 nm and 625 nm and 630 nm and 635 nm, for acne, and the wavelengths of 415 nm or 460-465 nm and 660 nm and 850-855 nm for MRSA.

It is an object of the LED light therapy device to comprise a system for light therapy which utilizes non-coherent light generated by an array of conventional light emitting diodes (LEDs) which are generally confined within a bandwidth of 415 nm to 940 nm. The diode array is configured in a matrix to direct the light onto a diffuse area of the user without utilizing an optical system or any intermediary material. The LEDs rest directly, or in close proximity, on the user's skin.

From the foregoing, it should be apparent that it is an aspect of the exemplary embodiments of the present invention to provide a light therapy system of the general character described which is not subject to the limitations of single wavelength devices.

It is an object of the LED light therapy device to provide a light therapy system of the general character described which is lightweight and portable.

It is an object of the LED light therapy device to provide a light therapy system of the general character described which is well suited for relatively low cost mass production fabrication and is a still further consideration of the present invention.

It is an object of the LED light therapy device to provide a light therapy system of the general character described which is simple in operation and convenient for home use.

It is an object of the LED light therapy device to overdrive the LED's to create heat that is conducted to the skin of the user to provide heat in addition to the light therapy. In some exemplary embodiments, a single resistor is used to consistently limit the current to all of the LED's, including LED's of different wavelengths, and provide both even illumination and heat.

It is another object of the LED light therapy device to provide a light therapy system of the general character described, which produces beneficial bio-stimulative effects.

It is another object of the LED light therapy device to provide a light therapy method of the general character described whereby non-coherent and non-monochromatic light within a general wavelength range of 415 nm to 940 nm is employed for photo-bio-stimulation.

It is still another object of the LED light therapy device to provide a light therapy method of the general character described which utilized non-coherent and non-monochromatic light emanating from conventional light emitting diodes.

Various objects, features, aspects, and advantages of the exemplary embodiments of the present invention will become more apparent from the following detailed description of preferred embodiments, along with the accompanying drawings in which like numerals represent like components.

DETAILED DESCRIPTION

Figure 1:
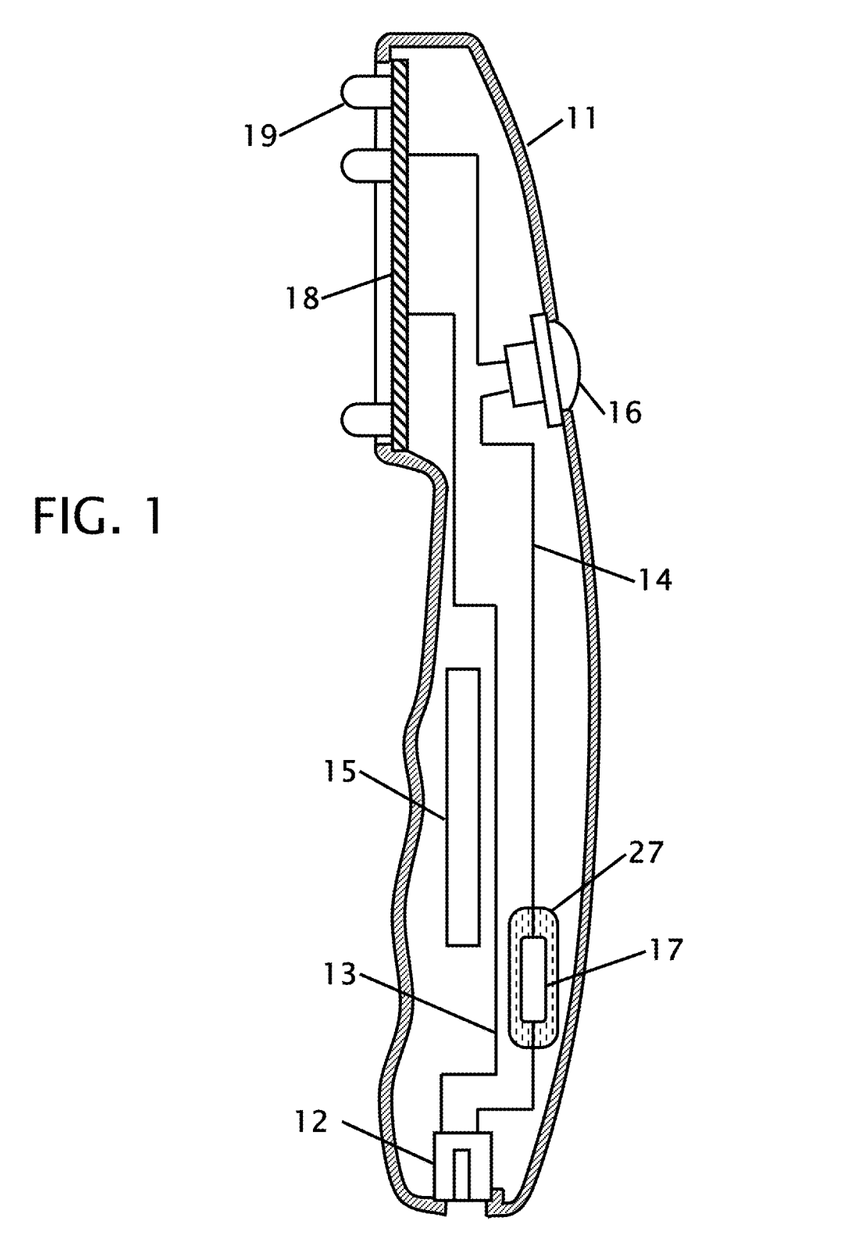
FIG. 1 shows a cross sectional view of a hand held version of the LED light therapy device, according to an exemplary embodiment.

FIG. 1 shows a cross sectional view of a hand held version of the LED light therapy device. The device includes an array of 12 to 600 light emitting diodes incorporated in 3-200 parallel circuits of 3, 4 or 5 in a series of conventional light emitting diodes (LEDs) configured to emanate an even distribution of light in the following wavelengths: 415 nm or 460-465 nm, 605 nm, 630 nm, 660 nm, 850-855 nm and 940 nm, depending on the design intent of the device. The selection for the different wavelength light emitting diodes based upon the intended therapy is shown and described in more detail FIGS. 5 and 6. While a particular number and array of light emitting diodes has been disclosed, more or less light-emitting diodes can be used in other larger or smaller designs.

In FIG. 1, the device is enclosed within a plastic housing 11. The device is energized by an external AC to DC 9-12 volt 300-500 mA power supply through a connector 12 to a negative lead 13 and a positive lead 14, through a current limiting resistor 17 then to the on/off switch 16 and finally to the rigid printed circuit board 18 that holds the different wavelength light emitting diodes 19. A weight 15 is preferably placed in the handle to provide balance to the device. The resistor 17 is positioned to eliminate thermal transfer from the resistor through the LED's because any heating from one or more resistors 17 provides uneven and inconsistent heating. The resistor 17 is also thermally enclosed 27 jacketed or otherwise covered to further disperse any heat away from the treatment area.

FIG. 1 comprises a cross sectional view through the device including a printed circuit board 18. The output of all of the light emitting diodes 19 is directed outward at right angles, or normal, to the circuit board 18 on which they are mounted, without lenses, mirrors, reflective surfaces, optical systems or any intermediary material between the LEDs and the skin of the patient.

Figure 2:
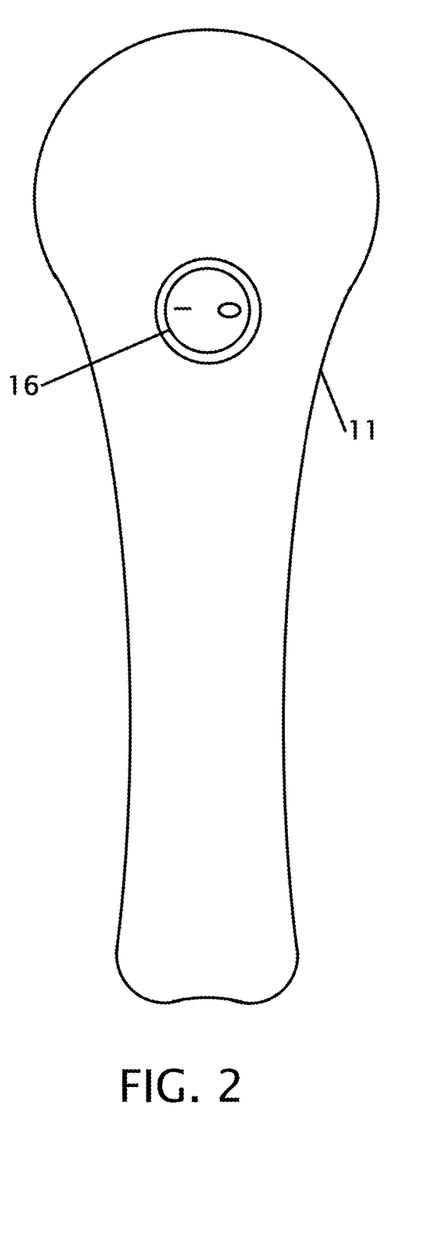
FIG. 2 is a top view of the device of FIG. 1, showing the location of an on/off power switch.
Figure 3:
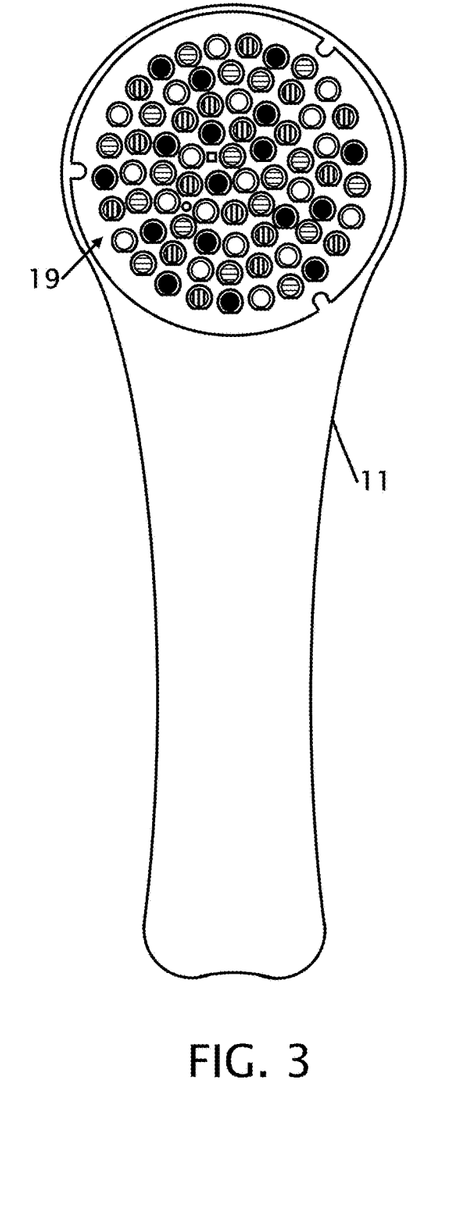
FIG. 3 is a bottom view of FIG. 1, showing an arrangement of the light emitting diodes arranged for multiple purposes.

FIG. 2 and FIG. 3 show a top view and bottom view, respectively, of the device showing the location of the on/off power switch 16 and an arrangement of the light emitting diodes 19 arranged for multiple purposes in the housing 11.

Figure 4:
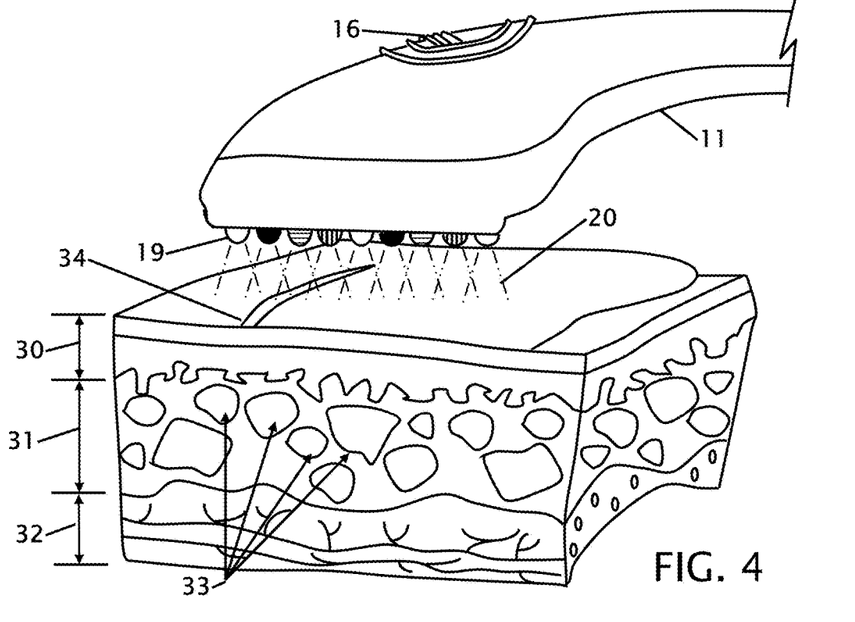
FIG. 4 shows the device of FIG. 1, in use with a cross section of skin tissue.

FIG. 4 shows the device in use with a cross section of skin tissue. The device has a housing 11 with an on-off power switch 16. LED light therapy is the use of specific types of light that give off energy that stimulates your cells, thereby increasing the production of collagen and elastin. In turn, this makes your skin firmer, less wrinkled, and younger looking. This is known as photo rejuvenation. The light emitting diodes 19 give off energy in the form of light 20. The light emitting diodes 19 are compact, durable, powerful, bright, efficient, and produce rejuvenating effects on the skin.

Skin is made up of 3 layers: the epidermis 30, the dermis 31 and the subcutaneous 32. The epidermis 30 is the outer layer made up of non-living cells that form your body's protective cover. These cells are constantly being shed and replaced by new ones. The new cells are made in the lower part of the epidermis 30. These are called Keratinocytes which produce the tough, fibrous protein called Keratin.

The next layer is the dermis 31. It is thicker and contains blood vessels, nerves and connective tissue. There are two main proteins in the dermis 31 or second layer of skin. The first main protein is collagen that makes up approximately ¾ of the dermis and is made up of this protein that is responsible for the strength and plumpness of the skin. The second protein is elastin, which is responsible mainly for the elasticity of the skin.

The next layer is the subcutaneous 32, it is the layer that contains the fatty tissues and stores energy, provides warmth and a cushion, etc.

People need certain wavelengths of light similar to the way plants need sunlight to thrive. Photo Rejuvenation produced by the device 11 translates the process of plant photosynthesis into the workings of human skin cells; thereby stimulating the body's own cells to build new proteins the same way plants use chlorophyll to convert sunlight into cellular building blocks.

Skin and other body tissues have the ability to absorb light and use it as a source of energy to stimulate cellular regeneration. The light rays 20 that are emitted from the device are beneficial for your skin, as they contain no UV rays. The problem with getting these same light rays from the sun is that you also get the harmful UV rays. These harmful rays can do more damage to your skin than good. With light emitting diodes, when the correct wavelengths of light are closely and intensely flowed into the body, collagen and elastin is produced in cells called Fibroblasts 33. Inside these cells is a smaller cellular structure called Mitochondria.

Mitochondria are responsible for converting nutrients into an energy carrier known scientifically as Adenosine Triphosphate (ATP). This (ATP) fuels the cell's activities; it gives the cells the needed energy to do their job. This is the reason Mitochondria are frequently referred to as the powerhouse of the cell. The device 11 sends light rays 20 into the fibroblast cells 33, which in turn excite the mitochondria into producing in some cases up to 10 times more ATP, but usually 2 to 4 times. This fuels the cell's activities, which causes more of the needed collagen and elastin to be produced, as well as other needed materials for the skin. The light rays 20 reduce or eliminate wrinkles 34 on the epidermis 30.

Figure 5:
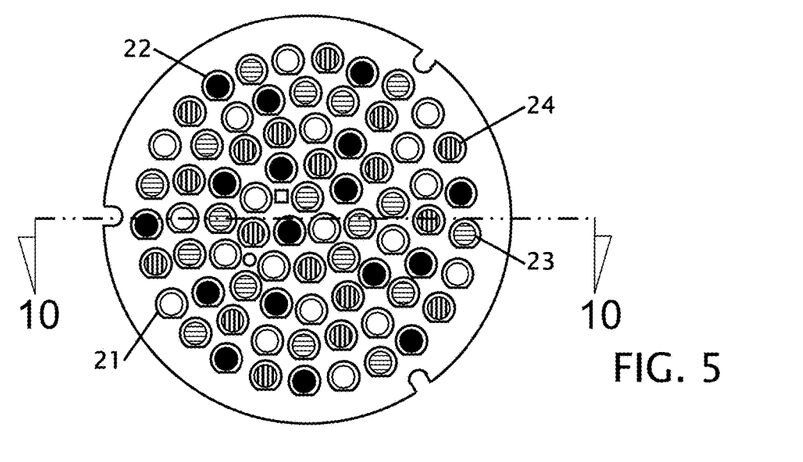
FIG. 5 is a bottom view of an exemplary embodiment showing an arrangement of the different wavelength light emitting diodes.
Figure 6:
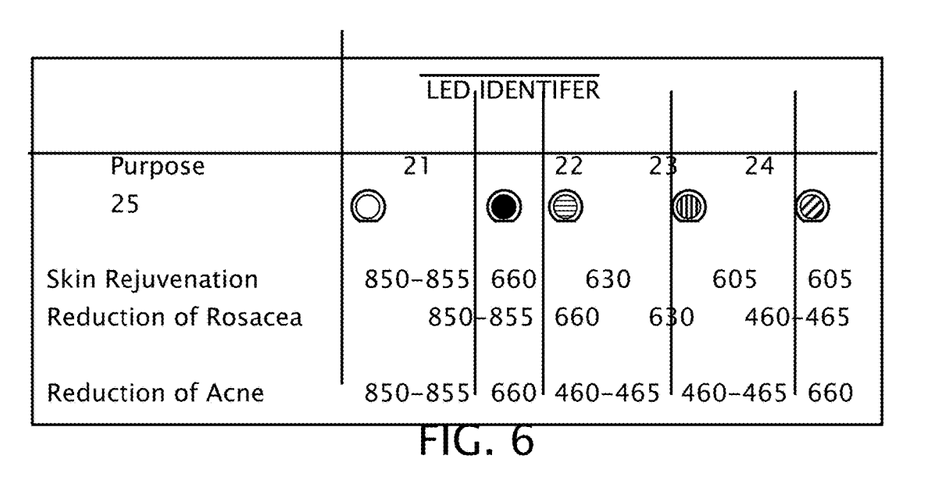
FIG. 6 is a table identifying the different colored light emitting diodes for four different intended purposes.

FIG. 5 is a bottom view of the device showing an arrangement of the different wavelength light emitting diodes. Depending upon the intended purpose of the device, different colored, or wavelength light emitting diodes 21-24 are used. In figure five the different colors or the array of light emitting diodes is shown. In FIG. 6, a table is shown identifying the different colored light emitting diodes 21-24 for four different intended purposes including but not limited to skin rejuvenation, reduction of rosacea, reduction of acne and therapeutic application.

Different wavelengths of light and combination of wavelengths of light have been shown to provide various treatments, including, but not limited to:

1. Wrinkles/anti-aging, age spots and to reduce pore size: 605 nm, 630 nm, 660 nm, and 850-855 nm.
2. Pain relief including arthritic pain: 630 nm, 660 nm, 850-855 nm, and 940 nm.
3. Treat acne and healing burn victims: 415 nm and 630 nm or 460 nm-465 nm, 660 nm and 850 nm-855 nm, or 415 nm and 630 nm, or 415 nm and 625 nm and 630 nm, or 415 nm and 625 nm and 630 nm and 635 nm may be used.
4. Rosacea: 460 nm-465 nm, 605 nm 630 nm, 660 nm, 850 nm-855 nm.
5. MRSA: 415 or 460-465 nm and 850-855 nm.
6. Swelling and inflammation of the brain caused by severe head trauma; heal the chest after open-heart surgery: 850 nm-855 nm.
7. Psoriasis+Eczema (used w/serum): 630 nm, 660 nm, 850 nm-855 nm, and 940 nm.
8. Post-op to reduce scarring, bruising, healing time, pain, inflammation and redness: 630 nm, 660 nm, 850-855 nm and 940 nm or 605 nm, 630 nm, 660 nm, and 855 nm.
9. Reverse blindness caused by diabetes: 630 nm, 660 nm, 850-855 nm, and 940 nm or 605 nm
10. Reverse macular degeneration: 630 nm, 660 nm, 850-855 nm, and 940 nm or 605 nm.
11. Heal sores in the mouth caused by chemo-therapy: 630 nm, 660 nm, 850-855 nm, and 940 nm.
12. Skin cancer: 630 nm. 660 nm. 850-855 nm. And 940 nm.
13. Bruising: 630 nm, 660 nm, 850-855 nm, and 940 nm.
14. Sinuses: 630 nm, 660 nm, 850-855 nm, and 940 nm.
15. Bells Palsy: 630 nm, 660 nm, 850-855 nm, and 940 nm or 605 nm, 630 nm, 660 nm, and 850-855 nm.
16. Heal the chest after open-heart surgery: 850-855 nm.
17. Help to regrow hair: 630 nm, 660 nm, 850-855 nm, and 940 nm.
18. Fiber-myalgia: 630 nm, 660 nm, 850-855 nm, and 940 nm or 605 nm, 630 nm, 660 nm, and 850-855 nm.
19. Relief of carpal-tunnel pain: 630 nm, 660 nm, 850-855 nm, and 940 nm.
20. Increased blood circulation: 630 nm, 660 nm, 850-855 nm, and 940 nm.
21. Age spots: 605 nm, 630 nm, 660 nm, and 850-855 nm.

The above wavelength listings are representative and may be varied for optimum treatment.

The plurality of light can have a small variation between the light frequencies, such as 625 nm, 630 nm, and 635 nm by using LEDs with different dispersion and intensities. These light frequencies 625 nm, 630 nm and 635 nm can be combined with a light frequency of 415 nm that kill bacteria, to provide optimal benefit.

Figure 7:
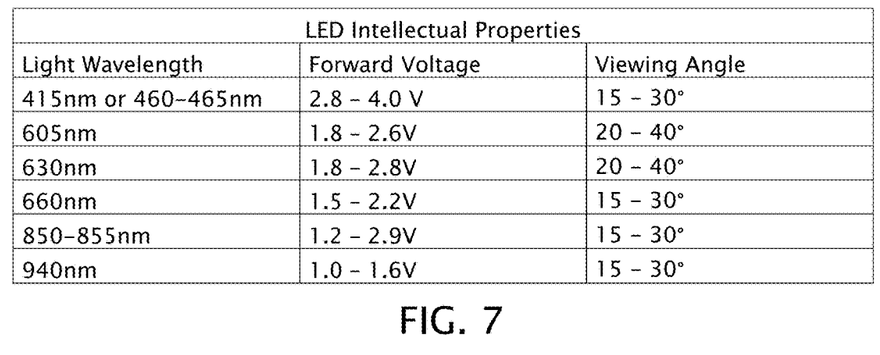
FIG. 7 shows a table with the different parameters of the LED's.

FIG. 7 shows a table with the different parameters of the LED's. This table shows the wavelengths of the LED's that are being used, the forward voltage of the LED's, and the viewing angle for each wavelength of light. The single resistor provides essentially the same voltage to all columns of three or more LED's.

Figure 8:
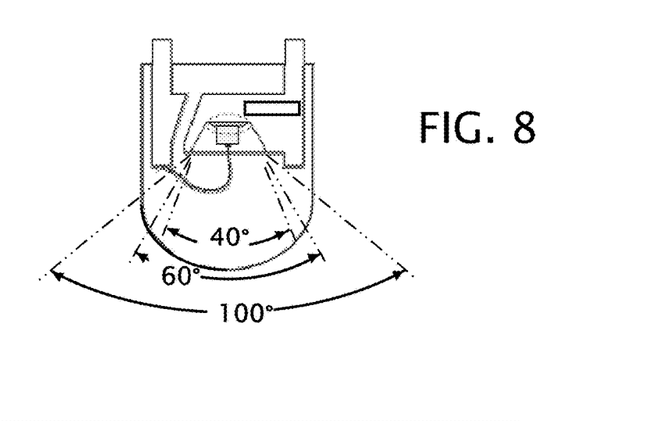
FIG. 8 shows a cross section of a single LED.
Figure 9:
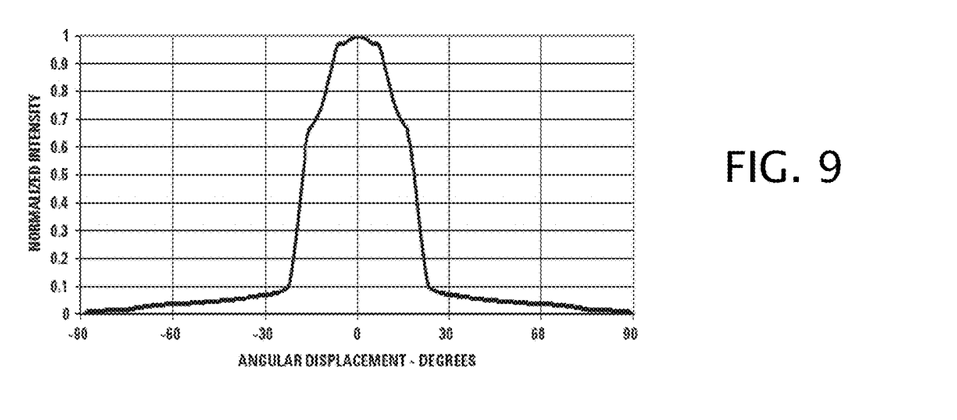
FIG. 9 shows the light dispersion of a typical LED with a 30 degree viewing angle.

FIG. 8 shows a cross section of a single LED. From the table in FIG. 7, the viewing angle of the 660 nm LED's are as small as 15 to 30°, while the 850 nm-855 nm LEDs have a viewing angle as large as 15-30°. The viewing angle is usually fairly evenly distributed and FIG. 9 shows the light dispersion of a typical LED with a 30-degree viewing angle. Referring back to FIG. 8, the viewing angles of 40°, 60° and 100° are shown to identify that the dispersion of light from the different colored LED's can be significantly different. This result in fairly focused light under some LED's where a particular wavelength of light, such as the 660 nm LED's may not completely cover the treatment area while the light from the 850 nm-855 nm LED's may completely cover the treatment area.

Figure 10:
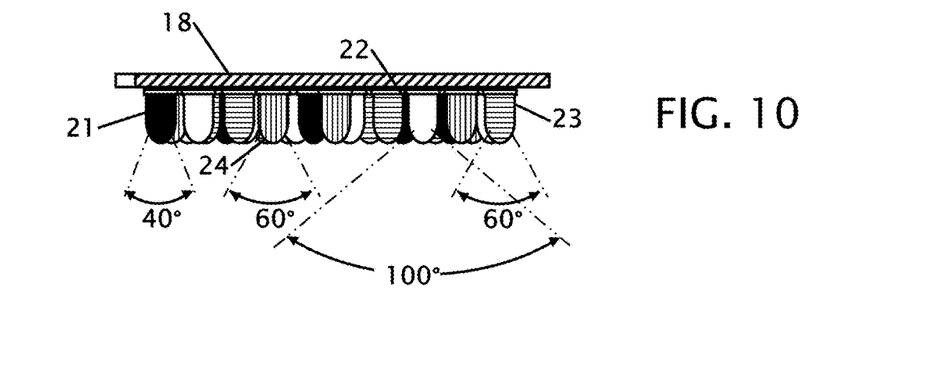
FIG. 10 shows a cross section view of the light emitting portion of the device from FIG. 5, taken along lines 10-10.

FIG. 10 shows a cross section view of the light emitting portion of the device from FIG. 5 taken along sectional lines 10-10. From this figure the different viewing angles of the different colored LEDs is shown. The narrow viewing angle of the 660 nm LEDs 21 is generously shown as 15-30°, while the viewing angle of the 850-855 nm LEDs 22 are shown as 15-30°. With a single treatment, complete light coverage with all of the LED light wavelengths may not be achieved, but multiple applications with the device placed in slightly different locations will provide even coverage in the aggregate. In addition, dispersion and reflection of the light caused by the dermis will further disperse and even light from narrow viewing angle LEDs.

Figure 11:
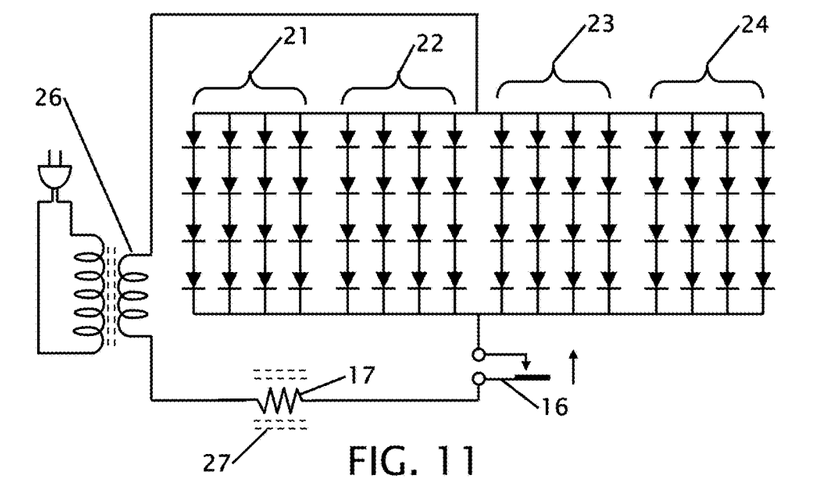
FIG. 11 shows an electrical diagram of a device of an exemplary embodiment.

FIG. 11 shows an electrical diagram of the device. A switch 16 connects the wall transformer power supply 26 to the remainder of the circuit. An AC to 9-12 volt DC power adapter 26 to provide operation of the light emitting diode circuits 21-24 powers the light emitting diode array. The AC to DC power adapter 26 provides the voltage and amperage required for optimal output and life of the light emitting diodes 21-24. In the preferred embodiment shown the light emitting diode array includes a plurality of diode circuits connected in parallel 21-24 with the diodes of each circuit being series connected. An electrical resistor 17 is positioned so as to current limit the current to the entire circuit board for the purpose or regulating current to the light emitting diodes and maintaining a comfortable operating temperature of the device. The effect of the light emitted is a function of each wavelength.

The value of the resistor 17 is carefully selected and tested based upon the light emitting diodes 21-24 that are selected and the operating voltage of the light emitting diodes. The selection of the resistor 17 is selected to overdrive the light emitting diodes such that they produce thermal heating. Overdriving the light emitting diodes provides a higher illumination intensity to more deeply penetrate the skin. The selection of the resistor must also be determined to minimize overheating to the skin. In the preferred embodiment the current limiting resistor is selected to cause a deliberate increase in said skin tissue temperature to between 97 and 106 degrees Fahrenheit when held continuously against or in close proximity to said skin tissue for a 15-minute period. The resistor 17 is positioned to eliminate thermal transfer from the resistor through the LEDs because any heating from one or more resistors 17 provides uneven and inconsistent heating. The resistor 17 is also thermally enclosed, jacketed or otherwise covered to further disperse any heat away from the treatment area.

A therapy protocol when using the device requires a minimum of about 2 to 5 minutes of exposure before relocating the device to another area of concern. This process is repeated in each area. This regimen can be performed daily until the desired appearance of the skin is achieved.

Figure 12:
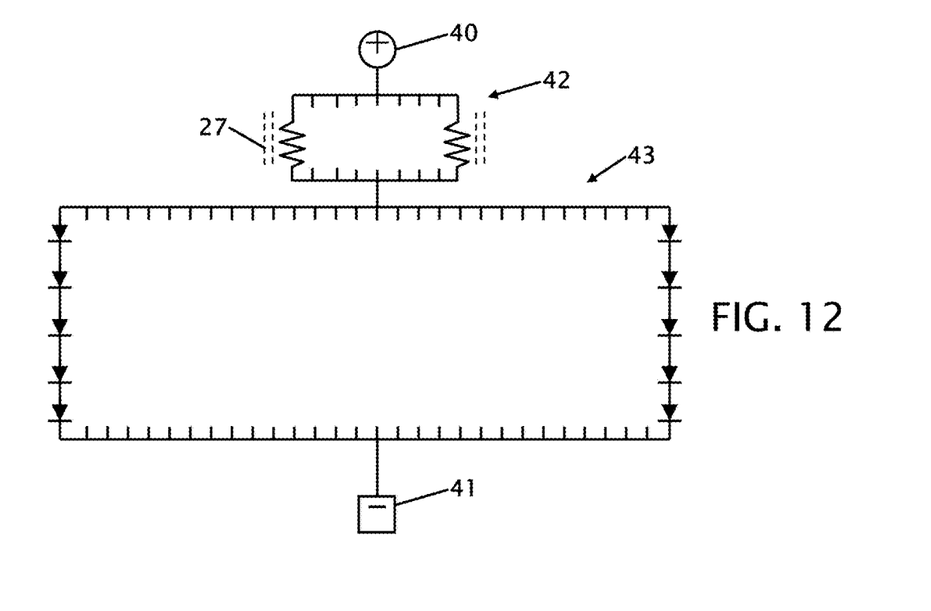
FIG. 12 shows an electrical diagram of a larger panel of light emitting diodes.
Figure 13:
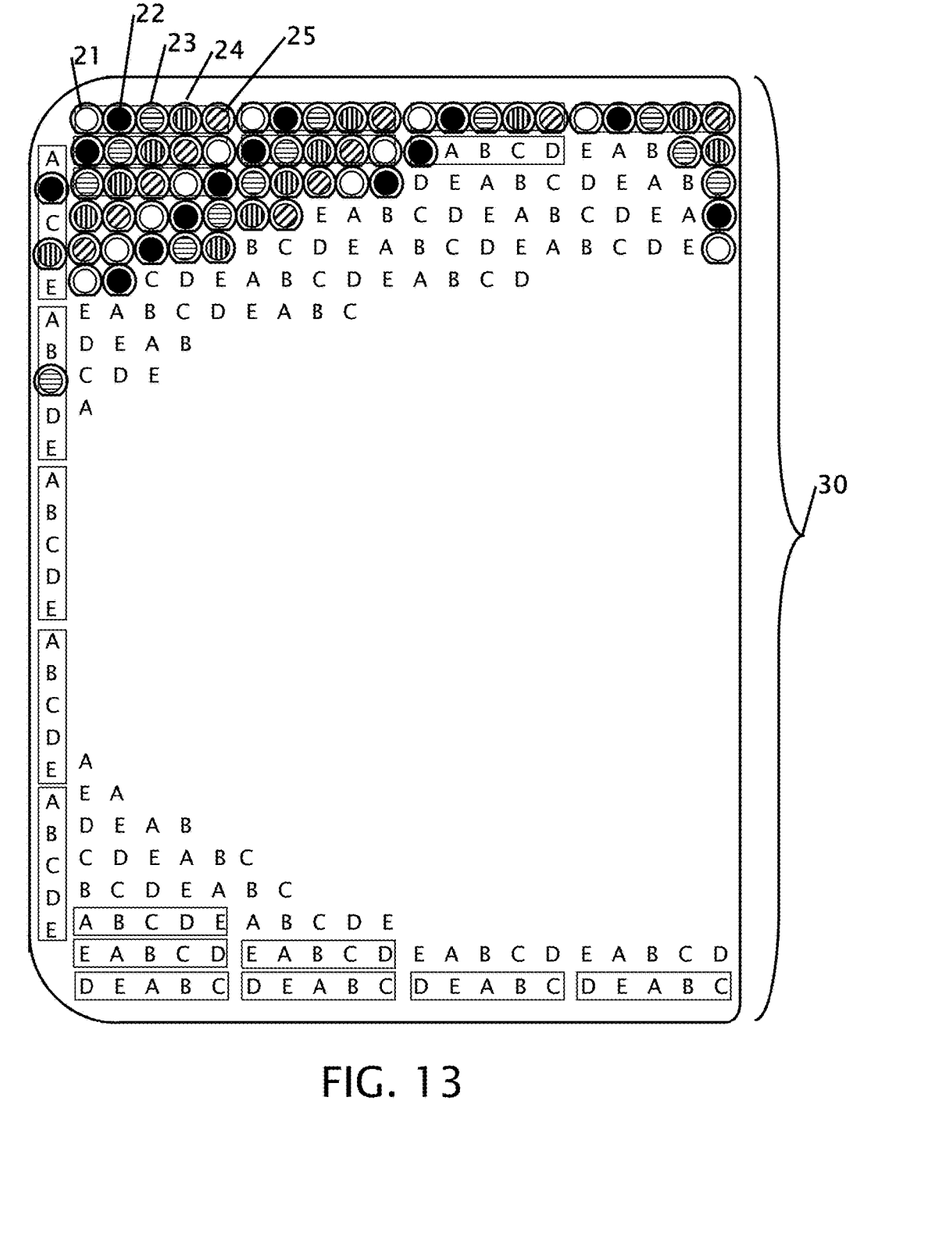
FIG. 13 shows a bottom view of the array of five different colored light emitting diodes, as identified in the electrical diagram of FIG. 12.

FIG. 12 shows an electrical diagram of a larger panel of light emitting diodes and FIG. 13 shows a bottom view of the array of five different colored light emitting diodes as identified in the electrical diagram of FIG. 12. In this circuit, an array of resistors 42 is used to minimize the physical thickness of the unit, but a single resistor could also be used. The resistor and light emitting diode circuit is connected to a positive terminal 40 and a negative terminal 41 from a 12-volt DC power supply of about 5.4 Amps. In one exemplary embodiment, the panel comprises of an array 43 of five different colored or wavelength light emitting diodes with 1130 or 1132 light emitting diodes 21-25. The 1130 or 1132 light emitting diodes are selected from the following groups of light emitting diodes 226 (415 nm or 460-465 nm, 605 nm, 630 nm, 660 nm, 850-855 nm, and 940 nm wavelength light emitting diodes) in a repeating pattern as shown in panel 30. While these quantities and wave lengths of light emitting diodes are disclosed, various different ratios and wavelengths are contemplated based upon the specific treatment application.

Figure 14:
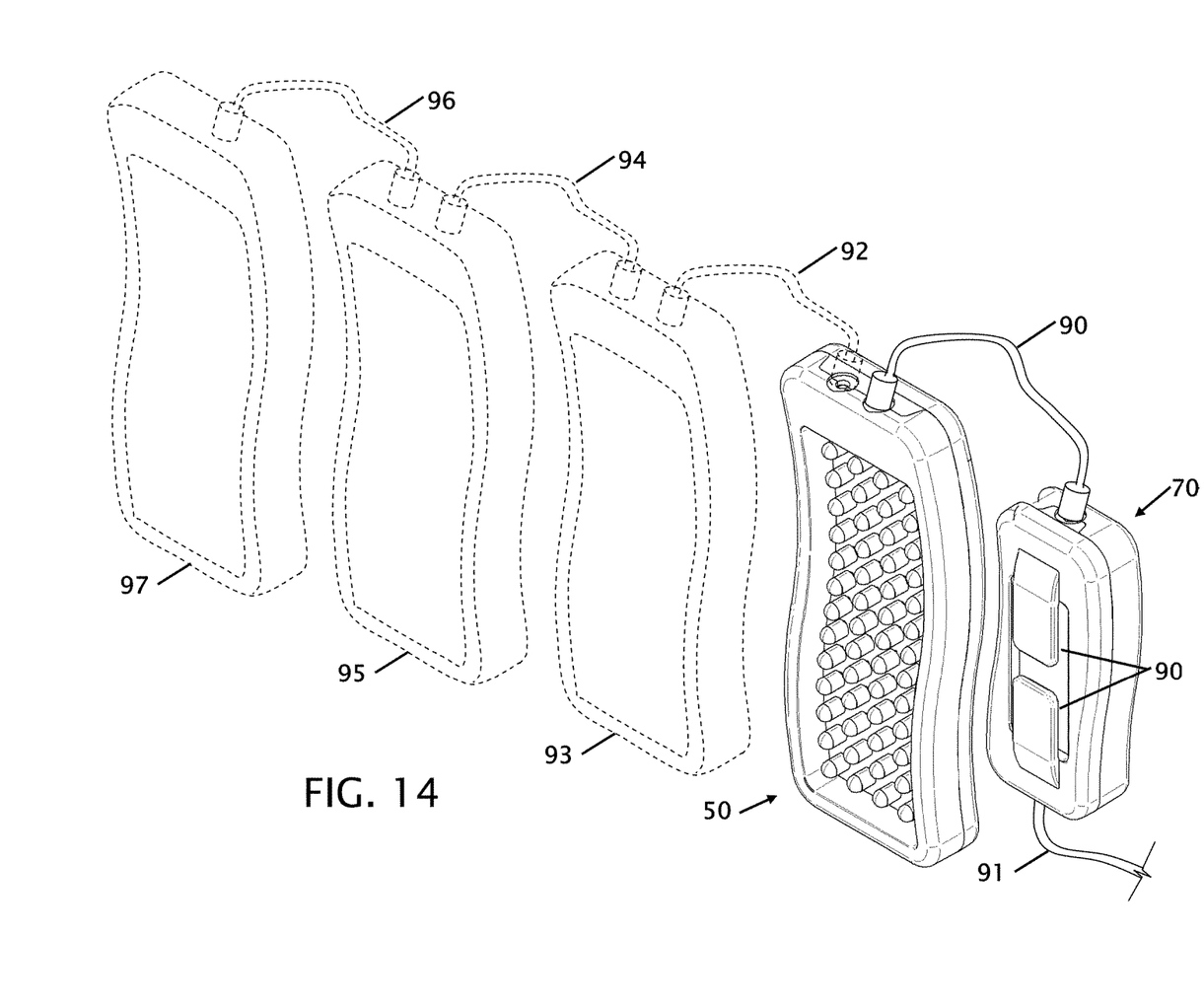
FIG. 14 shows a belt pain therapy device with a head unit and an LED module.

FIG. 14 shows a belt pain therapy device with a head unit 70 and an LED module 50. The head unit 70 is powered by an external power source 91 that powers both the head unit 70 and one or more LED modules 50, 93, 94, 95, and 97. The head unit 70 is connected to LED module 50 with wiring 90. In this example, four LED modules are daisy chained together with the first LED module 50 connected with wiring 92 to the second LED module 93. The second LED module 93 is connected to the third LED module 95 with wiring 84. The third LED module 95 is connected to the fourth LED module 97 with wiring 96. While this example shows four LED modules less than four can be connected together, and more than four LED modules may be connected, depending upon the power limitations of the incoming power 91 and the head unit 70, as well as the treatment to be provided. The connection wiring 90, 92, 94 and 96 allow the LED modules to be moved together or separated to provide optimal therapy of a single area or to multiple areas at the same time. The head unit 70 shows retention tabs 73 for retaining the head unit 70 on a belt (not shown in this figure).

Figure 15:
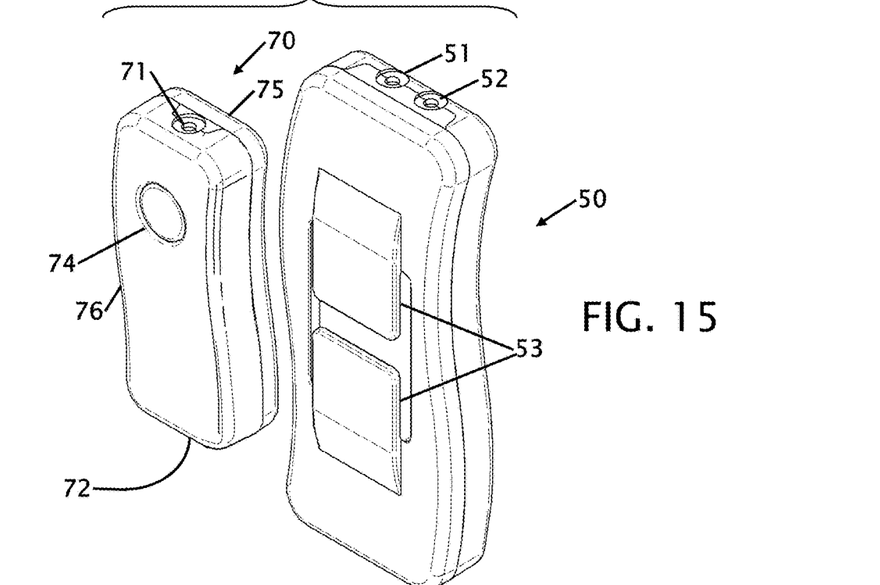
FIG. 15 shows an alternate view of the belt pain therapy device of FIG. 14.

FIG. 15 shows an alternate view of the belt pain therapy device from FIG. 14. In this figure the rear of the LED module 50 shows tabs 53 for securing the LED module 50 on a belt (no shown in this figure). A single button 74 on the head unit starts a timer within the head unit to operate the LED module(s) 50 for a pre-determined period of time. In the preferred embodiment the pre-determined period of time is 30 minutes, but the interval can be adjusted for a different interval of time. A second press of the button 74 will turn-off the LED module 50 and the timer. The bottom of the head unit 50 has a connection 72 for power to be applied to the head unit 50. The top of the head unit 50 has another connection 71 for connecting the head unit to a first LED module 50. The top of the LED module 50 has two connections 51 and 52 that are input and outputs to daisy chain power from the head unit 50 to additional LED module. The daisy chain connection between the LED modules can be made into and out of either connection 51, 52 because the regulation of incoming power is controlled within each LED module 50.

Figure 16:
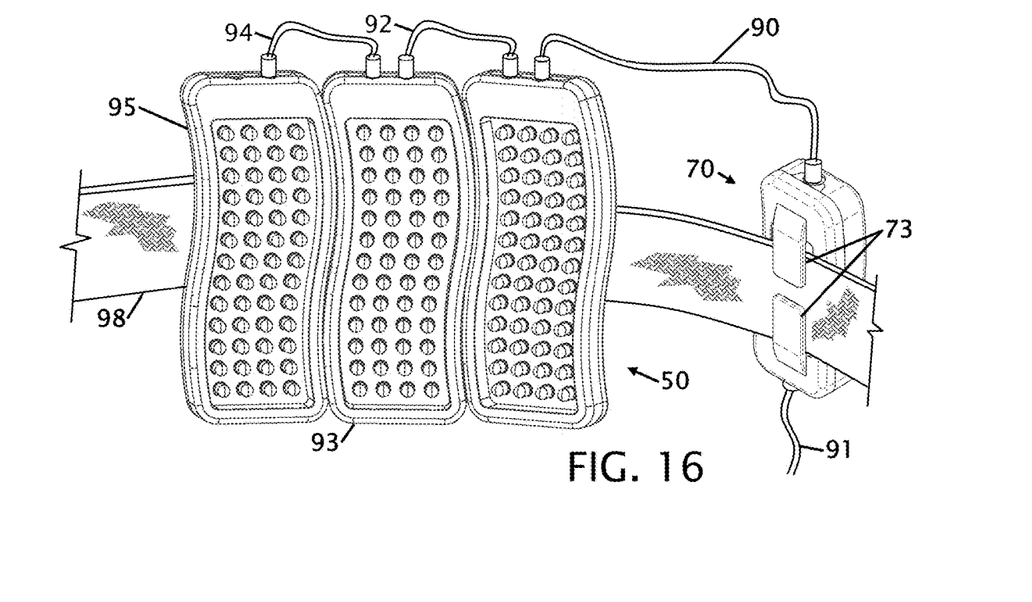
FIG. 16 shows a head unit and three LED modules of an exemplary embodiment.

FIG. 16 shows a head unit 50 and three LED modules 50, 93 and 95. It should be noted that the LED modules are configured with contoured sides to allow multiple LED modules to nest side-by-side and also to provide a smoother side-to-side transmission of light from the LED's. In this figure the three LED modules 50, 93 and 95 have a slightly curved orientation.

The power to the head unit 70 is received through wiring 91. The power from the head unit 70 is connected with cable 90 to the first LED module 50 and additional cables 92 and 94 daisy chain power to the two remaining units 93 and 85. The head unit 70 shown connected tabs 73 onto the belt 98. Both the head unit 70 and the LED modules 50, 93 and 95 can independently be translated along the belt 98 or can be individually removed or installed onto the belt 98.

Figure 17:
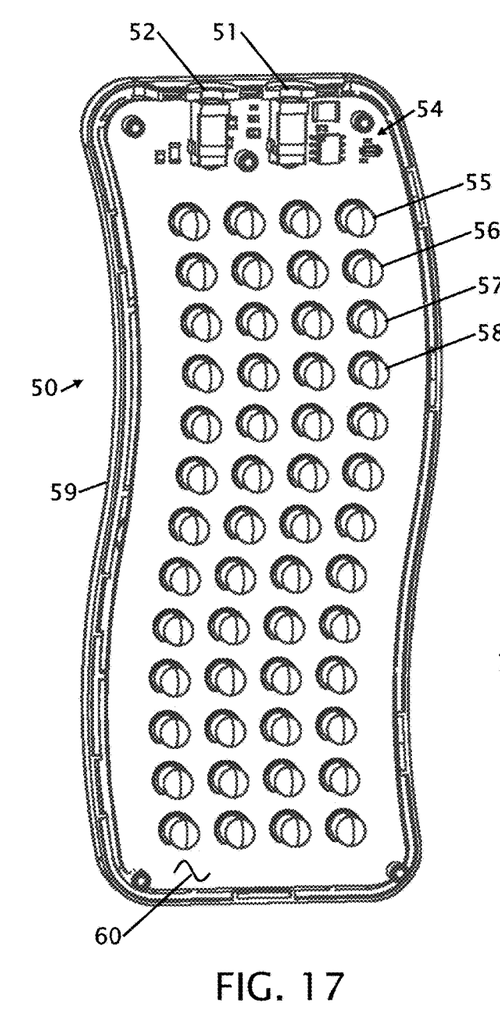
FIG. 17 shows a view of an LED module with the front housing removed.

FIG. 17 shows a view of the LED module 50 with the front housing removed. In this figure the circuit board 60 is shown with the multiple LED's 55, 56, 57 and 58 mounted on the circuit board 60 in the back housing 59. There are no intermediary lenses or heat sinks that dissipate light or heat from the LED's 55, 56, 57 and 58 to the surface of the skin of a user. The light therapy is provided without utilizing an optical system or any intermediary material. The LED's are arranged on an alternating pattern of colors that evenly distribute the plurality of light frequencies to treat skin. Each LED module 50, or 93, or 95 or 97 (93, 95 and 97 not shown in this figure) contains their own single current limiting circuit that is selected so that at least one of the LEDs 55, 56, 56, 57 and/or 58 is overdriven to increase light output of beyond normal operating intensity and to further produce thermal heat. The single current limiting circuit consistently limits the current to all of the plurality of different wavelength light emitting diodes to produce a skin temperate of between 97 and 106 degrees Fahrenheit from direct thermal conduction of said thermal heat from said light emitting diodes which are against or in close proximity to said skin tissue for predetermined period of time.

The daisy chain power connection 51 and 52 allow for multiple LED modules to be electrically connected together and controlled by the same head unit. The circuitry receives the power from the single head unit and uses a single current limiting circuit in each LED module so each LED module is separately and independently self-controlled. This allows different LED modules with different LED combinations to be utilized with the same head unit.

Figure 18:
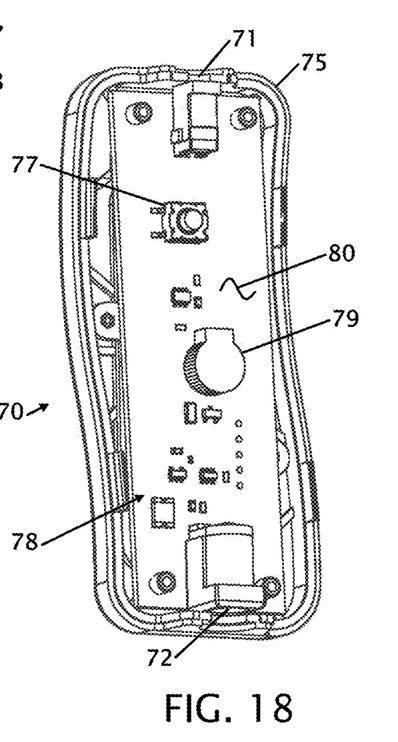
FIG. 18 shows a view of a head unit with the front housing removed.

FIG. 18 shows a view of the head device 70 with the front housing removed and the circuit board 80 in the rear housing 75. Power in connected to the head unit 70 through a first connector 72. The head unit 70 has a circuit board 80 with the switch 77 that provides regulated power out of the connector 71 that connects to one or more LED modules. Control device 79 is enclosed within the housing to adjust the duration for the treatment. The control circuit 78 regulates the incoming power to a level that will drive the LED modules.

Thus, specific embodiments of a therapy system utilizing light emitting diodes as a source of bio-stimulative have been disclosed. It should be apparent, however, to those skilled in the art that many more modifications besides those described in the exemplary embodiments are possible without departing from the inventive concepts herein. The inventive subject matter, therefore, is not to be restricted except in the spirit of the appended claims.

The invention claimed is:

1. A handheld tissue therapy device, the handheld tissue therapy device comprising:
   at least one enclosure;
   at least one circuit board secured within said at least one enclosure;
   said circuit board including an array of a plurality of different wavelength light emitting diodes configured to provide photodynamic stimulation of a surface and under lying layers of cells of skin tissue, wherein the stimulation of cells increases production of collagen and elastin;
   a power jack that receives DC power and a power switch electrically connected to said array of light emitting diodes though a single current limiting circuit to said plurality of different wavelength light emitting diodes; the single current limiting circuit being a single resistor; said current limiting circuit and a voltage supplied to said power jack is selected so that one or more of said plurality of different wavelength light emitting diodes is overdriven to increase light output of said light emitting diodes beyond normal operating intensity and to further produce thermal heat from said light emitting diodes, wherein the current limiting circuit consistently limits the current of said one or more of the plurality of different wavelength light emitting diodes to produce a skin temperature of between 97 and 106 degrees Fahrenheit from direct thermal conduction of said thermal heat from said light emitting diodes which are against or in close proximity to said skin tissue for a predetermined period of time; wherein said single current limiting circuit is selected to create a deliberate change in said thermal heating of said one or more of the plurality of different wavelength light emitting diodes while other wavelengths of LEDs are not overdriven in order to heat said skin tissue temperature to between 97 and 106 degrees Fahrenheit when held continuously against or in close proximity to said skin tissue for a 15-minute period; wherein there are no materials between the light emitting diodes and the skin of the patient; there are no heat sinks which dissipate light or heat from the LEDs; the single current limiting resister is positioned to eliminate thermal transfer from the resistor to the LEDs; wherein all of the light emitting diodes have wavelengths outside the UV range, and wherein the handheld tissue therapy device provides cell rejuvenation to treated cells of a person being treated by the handheld tissue therapy device.

2. The tissue therapy device according to claim 1 wherein said circuit board is configured to operate all of said plurality of different wavelength light emitting diodes with only a single positive and a single negative connection from said power switch and said current limiting circuit.

3. The tissue therapy device according to claim 1 wherein all of said light emitting diodes are contained on one or more printed circuit boards.

4. The tissue therapy device according to claim 3 wherein said one or more printed circuit boards have electrical connections for between 12 and 600 light emitting diodes.

5. The tissue therapy device according to claim 4 wherein said plurality of different colored light emitting diodes are placed in a repeating pattern.

6. The tissue therapy device according to claim 1 wherein said plurality of different wavelength light emitting diodes are connected in groups of at least two light emitting diodes connected in series with 4 to 200 circuits in parallel.

7. The tissue therapy device according to claim 1 wherein said light emitting diodes transmit light in the wavelengths of 630 nm, 660 nm, 850-855 nm, and 940 nm provides pain relief for a group including arthritic pain and carpal-tunnel pain, blood circulation, psoriasis, eczema when used with serum, post-op to reduce scarring, bruising, healing time, pain, inflammation and redness, healing sores in the mouth caused by chemo-therapy, to reverse blindness caused by diabetes, to reverse macular degeneration, to reverse loss of sight caused by stroke, to treat skin cancer, to reduce and eliminate bruises, to clear sinuses, to regrow hair and for Fibromyalgia.

8. The tissue therapy device according to claim 1 wherein said light emitting diodes transmit light in wavelengths selected from the group consisting of:
   the wavelengths of 415 nm and 630 nm,
   the wavelengths of 415 nm and 625 nm and 630 nm, and
   the wavelengths of 415 nm and 625 nm and 630 nm and 635 nm,
for acne, and wavelengths of 415 nm or 460-465 nm and 660 nm and 850-855 nm for MRSA.

9. The tissue therapy device according to claim 1 wherein said light emitting diodes transmit light in the wavelengths of 630 nm, 660 nm, 850-855 nm, 940 nm or 605 nm, 630 nm, 660 nm, and 850-855 nm for the purpose of treating Bells Palsy and Fibromyalgia.

10. The tissue therapy device according to claim 1 wherein said light emitting diodes transmit light in the wavelengths of 850 nm, or 850-855 nm for the purpose of therapeutic application for swelling and inflammation of the brain caused by severe head trauma or heal a patient's chest after open-heart surgery.

11. The tissue therapy device according to claim 1, further comprising
   light from different wavelength transmitting LED's, wherein the viewing angles allow the light from one or more LED's to overlap while the light from other LED's do not overlap.

* * * * *